(12) United States Patent
Schultz

(10) Patent No.: US 6,551,241 B1
(45) Date of Patent: Apr. 22, 2003

(54) INSTRUMENTS AND METHODS FOR PERFORMING PERCUTANEOUS SURGERY

(76) Inventor: Leonard S. Schultz, 11036 Boone Cir. South, Bloomington, MN (US) 55438

( * ) Notice: Subject to any disclaimer, the term of this patent is extended or adjusted under 35 U.S.C. 154(b) by 0 days.

(21) Appl. No.: 09/466,267

(22) Filed: Dec. 17, 1999

(51) Int. Cl.$^7$ .................................................. A61B 1/32
(52) U.S. Cl. ....................................... 600/192; 600/192
(58) Field of Search ................................ 606/192, 215, 606/151, 213; 623/23.64; 604/15, 523

(56) References Cited

U.S. PATENT DOCUMENTS

| | | | |
|---|---|---|---|
| 2,513,575 A | 7/1950 | Lombard | |
| 5,147,374 A | 9/1992 | Fernandez | |
| 5,154,179 A | * 10/1992 | Ratner | ........................ 600/420 |
| 5,176,692 A | 1/1993 | Wilk et al. | |
| 5,275,616 A | * 1/1994 | Fowler | ........................ 606/213 |
| 5,366,460 A | 11/1994 | Eberbach | |
| 5,370,660 A | * 12/1994 | Weinstein et al. | .......... 606/215 |
| 5,391,183 A | * 2/1995 | Janzen et al. | ................ 606/213 |
| 5,397,352 A | 3/1995 | Burres | |
| 5,456,720 A | * 10/1995 | Schultz et al. | ............ 623/23.64 |
| 5,496,345 A | 3/1996 | Kieturakis et al. | |
| 5,500,181 A | 3/1996 | Wang et al. | |
| 5,520,609 A | 5/1996 | Moll et al. | |
| 5,603,698 A | 2/1997 | Roberts et al. | |
| 5,607,465 A | 3/1997 | Camilli | |
| 5,634,931 A | 6/1997 | Kugel | |
| 5,643,178 A | 7/1997 | Moll et al. | |
| 5,690,668 A | 11/1997 | Fogarty et al. | |
| 5,702,416 A | 12/1997 | Kieturakis et al. | |
| 5,976,174 A | * 11/1999 | Ruiz | ........................... 606/213 |
| 6,099,518 A | * 8/2000 | Adams et al. | .............. 604/523 |

* cited by examiner

*Primary Examiner*—Michael J. Milano
*Assistant Examiner*—(Jackie) Tan-Uyen Ho
(74) *Attorney, Agent, or Firm*—Dorsey & Whitney LLP

(57) ABSTRACT

A method for repairing a defect. The method comprises accessing a percutaneous space adjacent the defect using a tubular member, placing an introducer adjacent the percutaneous space, and conducting tissue repair for the defect through the introducer.

34 Claims, 6 Drawing Sheets

US 6,551,241 B1

INSTRUMENTS AND METHODS FOR PERFORMING PERCUTANEOUS SURGERY

TECHNICAL FIELD

The present invention relates to methods and apparatus for performing surgical procedures, particularly minimally invasive surgical procedures. More particularly, it involves percutaneous surgical procedures and instruments for accomplishing such procedures, wherein embodiments of the invention include percutaneous herniorrhaphy including mesh reinforcement and/or gall bladder procedures.

BACKGROUND

A hernia is an abnormal protrusion of an organ, tissue, or any anatomical structure through a forced opening in some part of the surrounding muscle wall. For example, if a part of the intestine were to protrude through the surrounding abdominal wall, it would create a hernia—an abdominal hernia. A hernia in the groin area, also called the inguinal region, is known as an inguinal hernia.

Before a piece of intestine, abdominal cavity tissue, or other bodily tissue, called a hernial mass, makes its way through a weak spot in the muscle wall, it must first push its way through the peritoneum, which is the membrane that lines the abdomen. The hernial mass, however, does not typically tear and protrude through the peritoneum. Thus, when the intestine or hernial mass protrudes, it usually takes the peritoneum with it and it is covered by the peritoneum. The peritoneal covering surrounding the piece of protruding hernial mass is called a hernial Sac.

One known method for hernia repair involves the use of a mesh material or patch to line and support the hernial defect. The integrity and longevity of an abdominal wall hernia repair has been increased by the use of a large segment of mesh whose perimeter extends beyond the visualized margins of the defect. In one procedure, the segment of mesh may be placed within the preperitoneal space, which is the area located between the muscle wall and the peritoneum.

The use of mesh to repair hernial defects was first described and used in open incision medical procedures. Improvements in medical procedures have also resulted in the use of mesh in laparoscopic procedures. The open incision method was typically used as a final solution after other methods had failed, because it required a major incision with lengthy hospitalization for recovery, it caused significant post-operative pain, and it required at least a six week convalescence to achieve adequate scarring and strength. The laparoscopic method has provided improvements because no muscle damaging incision is necessary, only small puncture wounds are used instead of incisions, it can be done on an outpatient basis, and less post-operative pain and convalescence generally results to the patient. Both procedures, however, are operative techniques that require general anesthesia and can require significant recovery time. Additionally, the direct cost of the laparoscopic procedure remains considerably high because of the equipment that is necessary for the procedure.

An apparatus and method is needed for improving abdominal wall herniorrhaphy. Furthermore, such an apparatus and method is needed to perform a percutaneous surgical procedure that can reduce the trauma associated with open incision and laparoscopic procedures.

SUMMARY

One embodiment of the invention comprises accessing a percutaneous space using a tubular member, using the tubular member to place an introducer, and conducting tissue repair through the introducer. The tubular member may be positioned using anatomical landmarks, and the desired location of the tubular member may be assessed by means of contrast prior to placing a guide wire. After the guide wire is placed, the tubular member may be removed and replaced with a dilator and an introducer. The dilator is removed, and a form or a balloon is advanced into the preperitoneal space. The balloon's shape may be varied to approximate the desired shape of the space near a defect to be repaired. The balloon may also function as a carrier of a mesh for repairing the defect, and it may be a residual or removable balloon. The method and devices of the invention may be used to repair hernial defects as well as other anatomical defects.

When the defect is repaired, i.e., the mesh, and/or a curable filling material, is deposited, the stem or guide wire of the tubular, member (e.g., catheter), any balloon remnant and the introducer may be removed. Closure of the single puncture and a simple dressing complete the procedure.

Apparatuses or instruments for the method of the present invention include a catheter-like delivery device and a balloon for delivery-thereby. More particularly, the apparatus may include a tubular member (e.g., catheter, needle trocar or the like), a guide wire, a dilator (if required), an introducer and a balloon. The balloon may be of any desired shape and size as long as it passes through the selected introducer.

Other features and advantages of the present invention will become more fully apparent and understood with reference to the following description and the accompanying drawings and claims.

DETAILED DESCRIPTION

With regard to fastening, mounting, attaching or connecting the components of the present invention to form the apparatus of the invention, unless specifically described as otherwise, such are intended to encompass conventional fastening means and methods suitable for use with metallic, plastic and/or synthetic and natural elastomeric materials (e.g., threaded members, pins, etc.). Such fastening means and methods include adhesives, friction fitting, chemical and sonic welding, heating, deformation and the like. Unless specifically otherwise disclosed or taught, materials for making the components of the present invention are selected from appropriate synthetic and natural elastomeric materials such as silicone, latex, silastic and the like, metal or plastics (e.g., polypropylene or polytetrafluoroethylene). Appropriate forming methods including casting, dipping, extruding, molding and the like may be used.

Any references herein to front and back, right and left, top and bottom, upper and lower and horizontal and vertical are intended for convenience of description, not to limit the method or apparatus of the present invention or components thereof to any one positional or spacial orientation.

Figure 1:
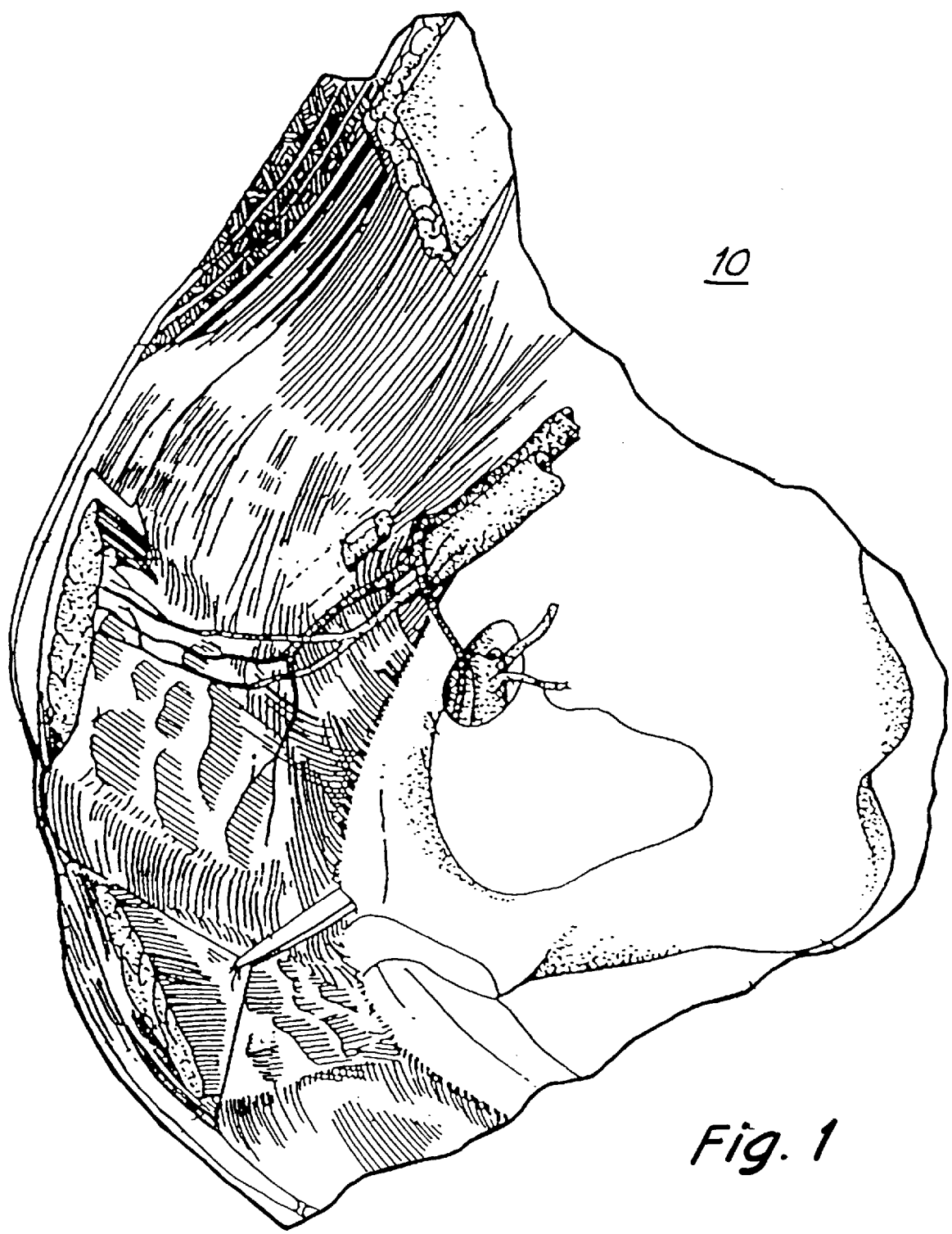
FIG. 1 is a fragmentary pictorial view of the interior of the abdomen of a patient with viscera removed.
Figure 2:
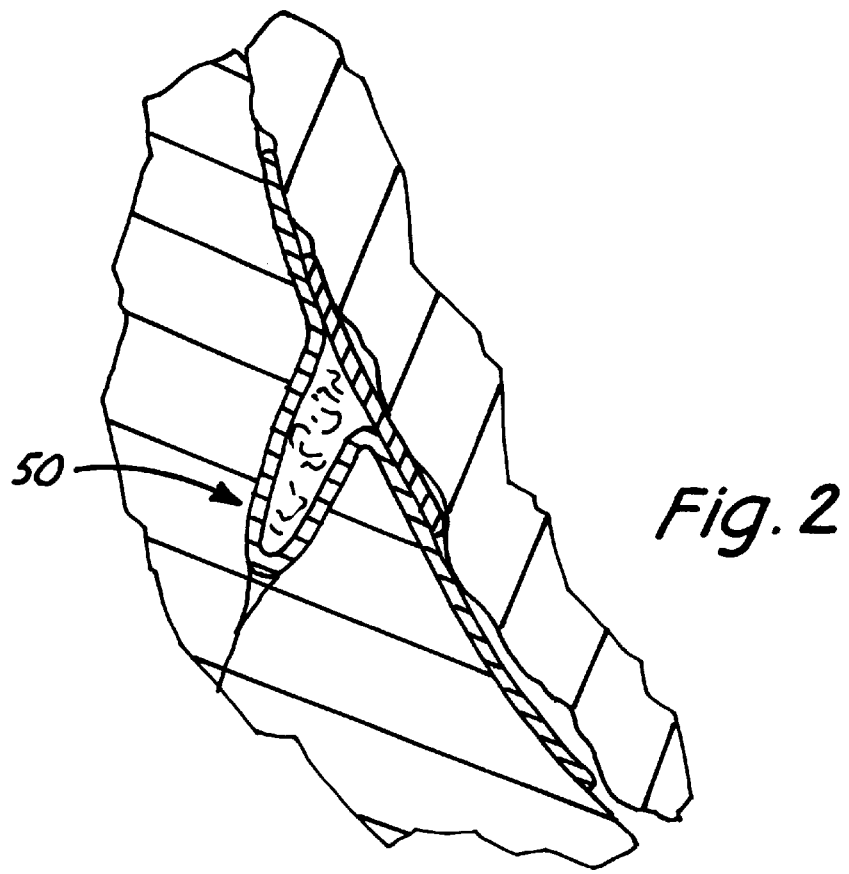
FIG. 2 is a sectional view of a mesh patch used in accordance with the present invention inserted into an anatomical defect.
Figure 3:
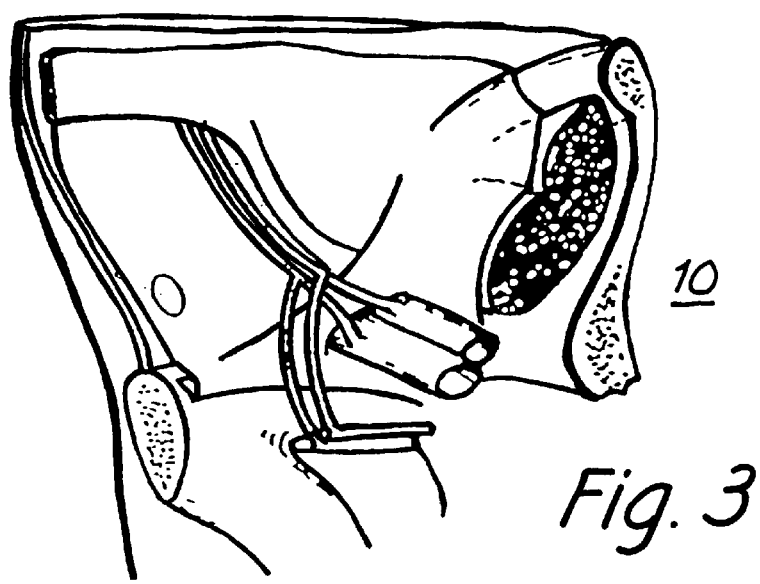
FIG. 3 is fragmentary view of a portion of the abdomen of a patient.

FIGS. 1 and 2 are provided to depict one field of use of one embodiment of the present invention, i.e., repair of hernia. FIG. 1 shows the interior of the abdomen 10 of a patient with viscera removed, and FIG. 2 shows a form 50 of an embodiment of the invention inserted into an anatomical defect. The present invention, however, may also be used for other percutaneous surgical procedures, and it may be used for abdominal, thoracic, or diaphragmatic hernia repair, and it may also be used for repair of other defects.

Figure 4:
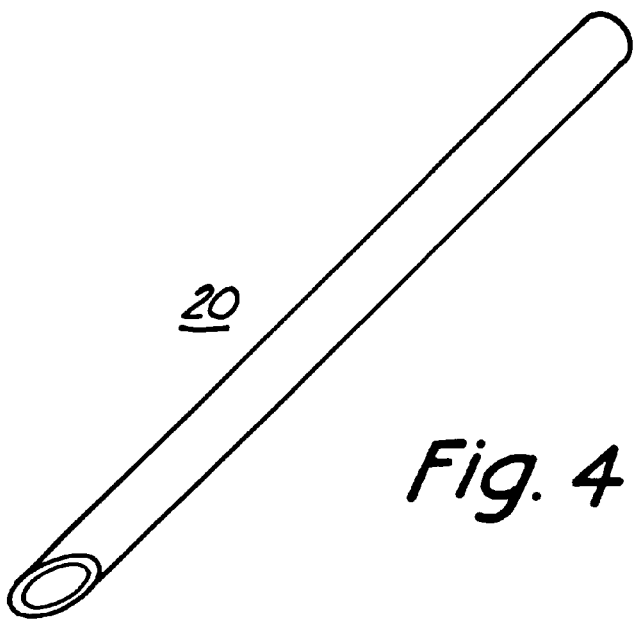
FIG. 4 is a perspective view of an introducer used in accordance with the present invention.

One embodiment of the invention is an apparatus or an instrument set for performing percutaneous surgical procedures. This apparatus or instrument set may comprise a tubular member for accessing a percutaneous location and an introducer for placement adjacent to the percutaneous location. The tubular member may be selected from the group consisting of catheters, needles and trocars. In this embodiment, the introducer may be placed through the tubular member and a selected percutaneous surgical procedure may be conducted through the introducer. The tubular member may be positioned using anatomical landmarks to place the tubular member in the proper space, which may be between the peritoneum and muscle. To aid in placing the tubular member, any method or device known by an interventional radiologist may be used, including injection of contrast with either fluoroscopy or imaging technology 15. Although different introducers may be used within the scope of the invention, one sample introducer 20 is the longitudinal and tubular device depicted in FIG. 4. FIG. 4 also depicts an embodiment of a tubular member 20 that may be used as part of the invention, which may be of a similar shape to the introducer. The apparatus or instrument set may also include a form 50 for insertion through the introducer, wherein a filling material may be deposited adjacent to the form 50. The term "form" will be used in this specification to refer to any patch, balloon, mechanism, or body that may be placed adjacent the defect to repair the defect, or to shape a prosthesis for repairing the defect. In one embodiment, at least a portion of the form 50 dissolves after the filling material is deposited.

In one embodiment, the form may comprise a prosthesis 60, which may form a patch such as a mesh patch, and a carrier 70 for the prosthesis. In another embodiment, the form 50 may comprise a prosthesis 60, such as a mesh patch or any patch known to those skilled in the art, that may be used without a carrier 70. A variety of meshes known to those skilled in the art may be used within the scope of this invention for the prosthesis. See U.S. Pat. No. 5,634,931, issued to Kugel on Jun. 3, 1997, and U.S. Pat. No. 5,456,720, issued to Schultz et al. on Oct. 10, 1995, which describe various mesh materials and are hereby incorporated by reference into this specification. The Schultz et al. and Kugel patents describe implantable hernia mesh patches that are intended for permanent placement within a patient's body. These meshes, as well as others known to those skilled in the art, repair and reinforce the area of the hernial defect.

The form 50, also called the access device, may be either hollow or solid and may be either a single piece or multiple pieces. The form 50 may also contain directional wires or preset curves. In one embodiment using a carrier 70 along with a prosthesis 60, the carrier 70 may be constructed of biocompatible material. The prosthesis 60 may be located at or near one end of the carrier 70. The prosthesis 60, which is the device used to repair the hernial defect, may be an integral part of the carrier 70 or it may be a separate piece attached to or contained within the carrier 70. In use, the prosthesis 60 may be detached from the carrier 70 and left within the hernial defect. The prosthesis 60, therefore, may be located near or may constitute the leading end of the carrier 70 such that it may be deposited in or over the hernial defect. The prosthesis 60, contained as a part of the form 50, may be placed within the preperitoneal space in order to repair the defect.

In one embodiment, the carrier 70 may be an expandable device of predetermined shape with its final volume and size designed to fit within the preperitoneal space. One purpose of the carrier 70 is to separate tissue planes to a size sufficient to contain the prosthesis 60.

Figure 5:
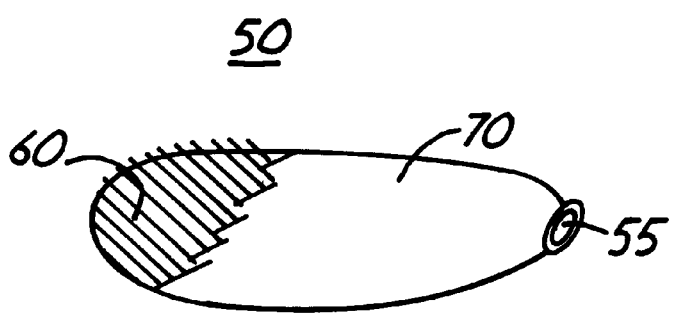
FIG. 5 is a perspective view of a balloon that may be used in accordance with the present invention.

In one embodiment, the carrier 70 may be a balloon, and the prosthesis 60 may be a mesh portion. A variety of balloons known to those skilled in the art may be used within the scope of the invention; one such balloon is depicted in FIG. 5 with numeral 70. See also U.S. Pat. No. 5,702,416, issued to Kieturakis et al. on Dec. 30, 1997, which discloses a balloon suitable for use with this invention, and is incorporated herein by reference. The mesh portion may either be carried by the balloon, integrated with the balloon, contained within the balloon, on the outside of the balloon, or may form the structure of the balloon itself. The material forming the prosthesis may be either continuous or perforated, and either permanent or dissolvable. Examples of materials that may be suitable for the prosthesis include stainless steel, polypropylene, polyesters, polytetrafluoroethylene, polyglactin, or polyglycolic acid. The prosthesis may also be readiopaque or its perimeter may be outlined with radiopaque material. After being, deposited adjacent to, within or over the hernial defect, the prosthesis 60 may remain in position, while a portion of it may dissolve. Alternatively, the expanded prosthesis 60 may be left in place to repair the defect.

In operation, the percutaneous surgical procedure for repairing a defect of the present invention may comprise accessing a preperitoneal location with a tubular member 90, placing a guide wire 95 through the tubular member 90, positioning an introducer over the guide wire 95, and inserting a form 50 or carrier 70 through the introducer to a position adjacent to the defect, whereby the carrier 70 serves to repair the defect. The form 50 may be collapsed and tightly compacted for advancement through the introducer and preperitoneal space to the defect. Accessing the preperitoneal location, which may be deep in the site of the hernia within the abdominal wall, may be accomplished using anatomic landmarks which guide the placement and direction of the tubular member 90 or trocar needle. Once the guide wire 95 is placed through the tubular member 90 and the tubular member 90 is removed, a dilator may be used to aid in the placement of the introducer. After placement of the introducer, the dilator may be removed. The carrier 70 may be tightly compacted and/or collapsed during placement through the introducer to the hernial defect.

In one embodiment, the percutaneous surgical procedure may comprise depositing a filling material through the introducer into the carrier 70. Once the carrier 70 is placed adjacent to the hernial defect, air or a liquid or semi-liquid material, such as saline, may be injected into the carrier 70 via a channel so that the carrier 70 will form a predetermined volume and shape. In this manner, the carrier 70 will both define the non-vascular tissue space in which the prosthesis 60 will be placed and it will deposit the prosthesis 60 within that space. In this embodiment, the carrier 70, which may be a balloon, may be expanded to approximate the desired shape of the space adjacent to the hernial defect, which may be circular, ellipsoid, rectangular, square, or a combination of geometries. In one embodiment, a slurry of biologic and/or plastic material may be used to "set up" to the shape of the balloon's dimensions, and the balloon may then dissolve leaving a mesh or mass of a desired size and shape in place. The prosthesis 60 may be deposited over the hernial defect through use of the carrier 70. After being deposited within or over the hernial defect, the prosthesis 60 may remain in position, while a portion of it may dissolve. Alternatively, the expanded prosthesis 60 may be left in place to repair the defect. In another embodiment, the prosthesis 60, which may be mesh, will remain in place to repair the hernia while the carrier 70, which may be a balloon, may dissolve or be withdrawn.

In another embodiment, the balloon itself may be made of a mesh material on one side with regular balloon material on the other side. After placement of the mesh portion of the balloon over the hernial defect, the nonmesh portion of the balloon could either be removed or could dissolve such that the mesh portion of the balloon would remain in place to repair the hernial defect. Upon completion of placement of the prosthesis over the hernial defect, the introducer and wire may be removed, along with any portion of the carrier that is not intended to remain within the patient's body. A simple dressing of the skin may then complete the operation.

Figure 6:
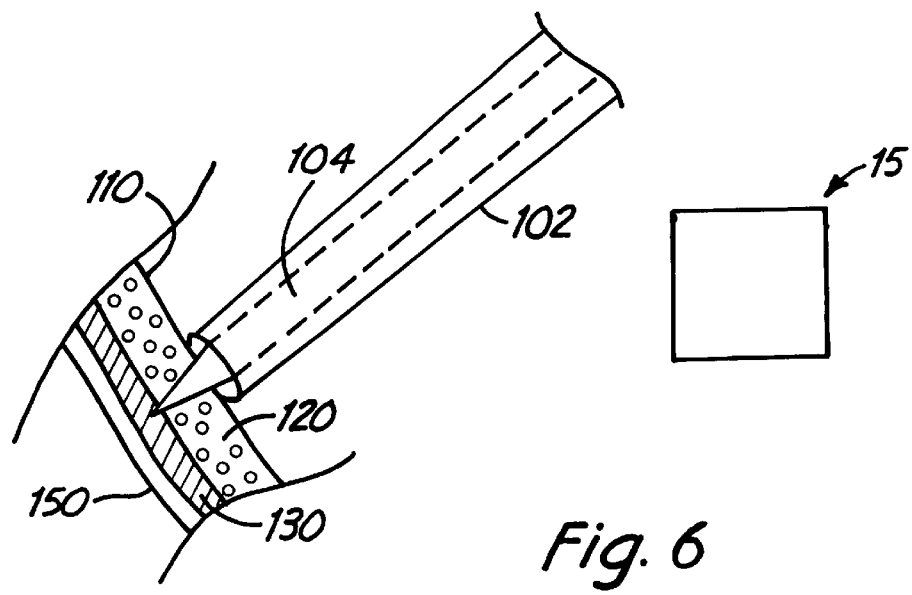
FIG. 6 is a perspective view of an trocar and an obturator passing through skin, fat, and muscle.
Figure 7:
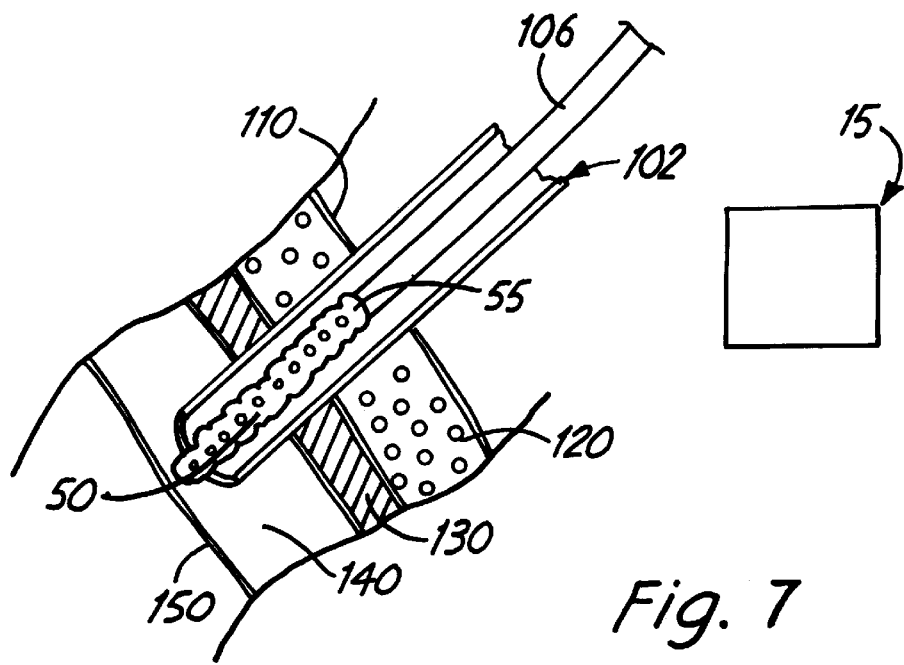
FIG. 7 is a perspective view of a form of the invention being placed through a trocar.

FIGS. 6–9 depict one embodiment of a method and instruments of the invention in use for the placement of a form 50 to repair a defect 100. FIG. 6 illustrates a trocar 102 with a sharp obturator 104 passing percutaneously through the skin 110, fat 120, and muscle 130 of the patient. The obturator 104 stops before the peritoneum 150 so that the preperitoneal space 140 may be accessed. In FIG. 7, the obturator 104 has been removed and the trocar 102 is in place as it opens the preperitoneal space 140. A placement rod 106 may be used to place the form 50 in place. The form 50, which may be a carrier 70 with a mesh patch 60 or prosthesis, is shown in a collapsed shape in FIG. 7 passing through the trocar 102, and the form 50 may contain a fastener 55 that attaches the form 50 to the placement rod 106. The fastener 55 may be a friction fit section, a twist section (e.g., threaded, bayonet, etc.), or any type of fastener known to those skilled in the art to removably attach the form 50 to the placement rod 106. The placement rod 106 may, therefore, have a complementary fastener for attachment to the form 50.

Figure 8:
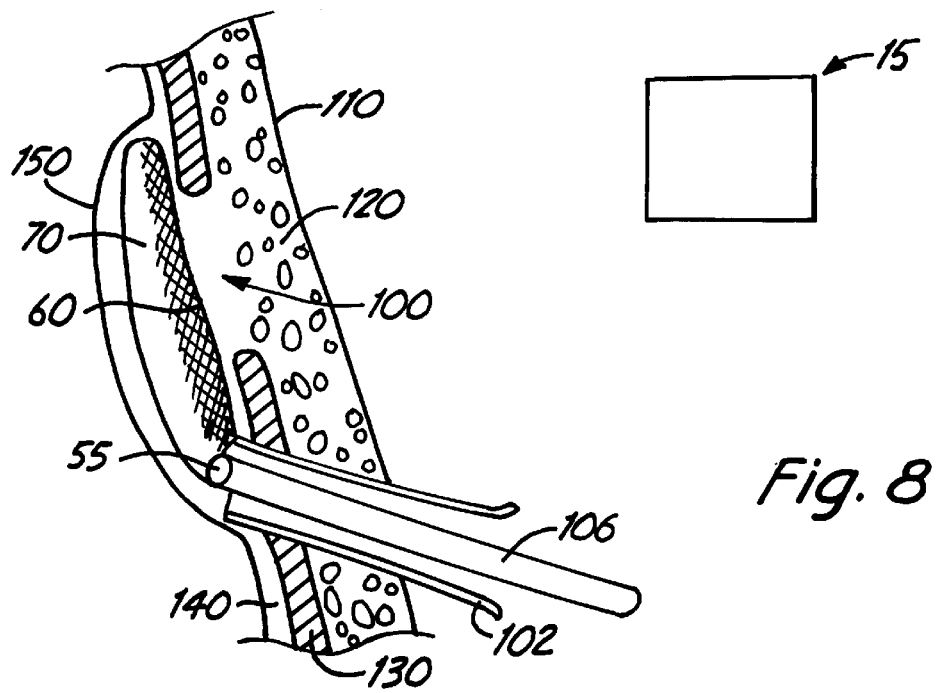
FIG. 8 is a perspective view of the placement of the form in one embodiment of the invention.
Figure 9:
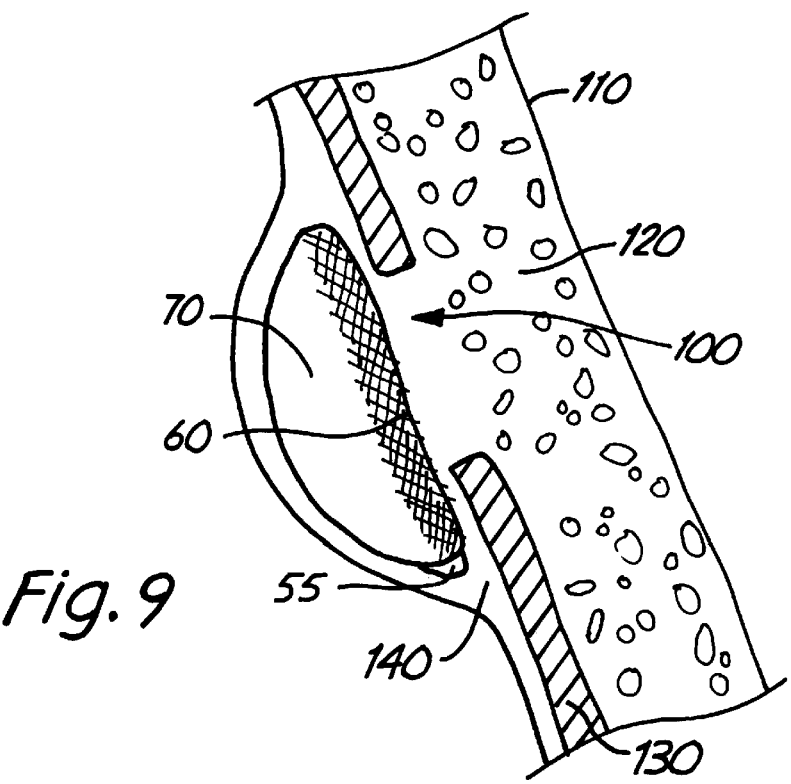
FIG. 9 is a perspective view of the form after placement to repair a defect.
Figure 10:
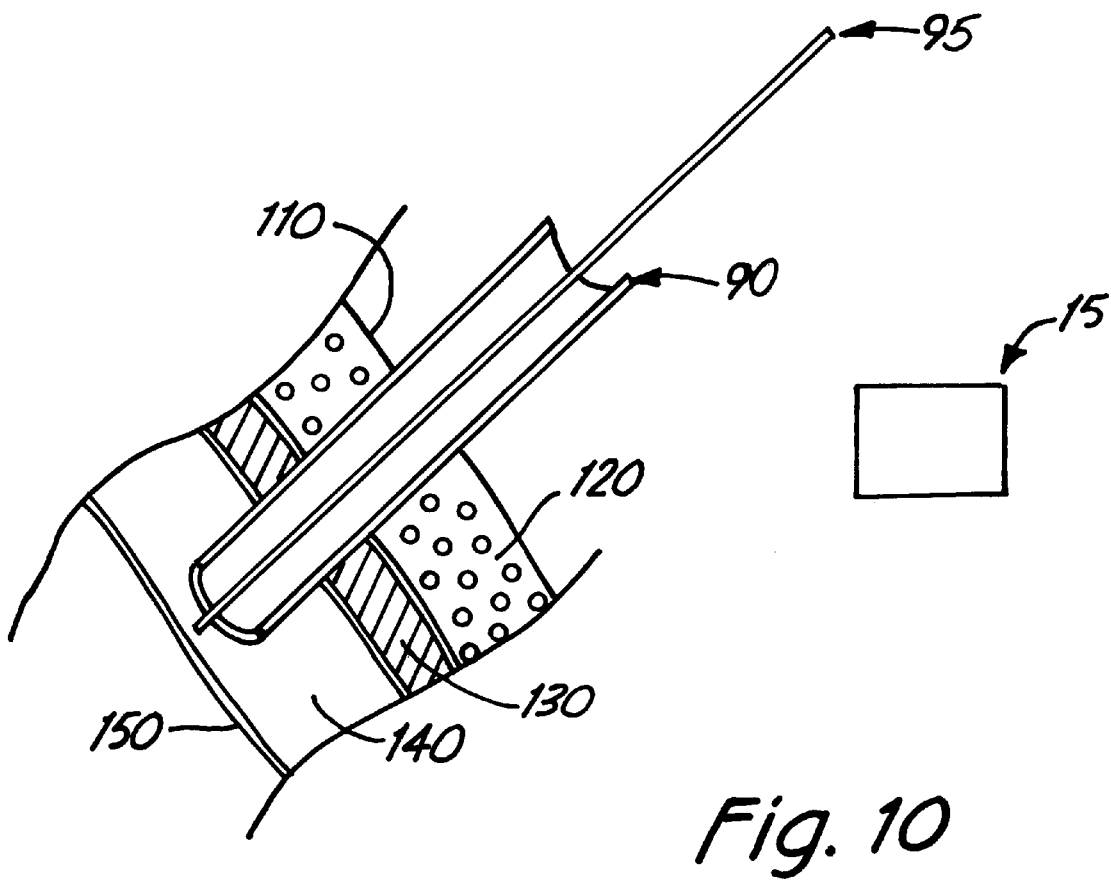
FIG. 10 is a perspective view of a guide wire placed through a tubular member.

In FIG. 8, the form 50, which is shown as a balloon or carrier 70 with a prosthesis 60 or mesh patch, is being placed over the defect 100. The placement rod 106 is used to position the carrier 70 and prosthesis 60 over the defect 100 and between the defect 100 and the peritoneum 150 so that the carrier 70 and prosthesis 60 are in the preperitoneal space 140. The carrier 70 with prosthesis 60 may then be detached from the placement rod 106 in any manner known to those skilled in the art. In one embodiment, a twisting motion may be used to detach the carrier 70 with prosthesis 60 from the placement rod 106. The placement rod 106 may then be removed, along with the trocar 102, and the skin may be closed to complete the procedure so that the defect 100 is repaired. In one embodiment using a balloon as the carrier 70, the balloon is an integral part of the mesh patch, which may be used as the prosthesis 60. The balloon may, in one embodiment, be made of a suitable material so that it dissolves, and the mesh patch may also be made of a material so that it dissolves over time. In other embodiments the balloon may not be dissolvable and/or the mesh patch may not be dissolvable. FIG. 9 illustrates the form 50, which is a carrier 70 and a prosthesis 60 in the depicted embodiment, placed in the preperitoneal space 140 to repair a defect 100. The preperitoneal space 140 may be accessed using any method known to those skilled in the art, such as artificial vision, including magnetic resonance imaging ("MRI") or nuclear magnetic resonance imaging ("NMR").

Design examples of the methods of the present invention are described above and herein, along with examples of instruments for accomplishing the methods. While the present invention has been described with reference to several embodiments thereof, those skilled in the art will recognize various changes that may be made without departing from the spirit and scope of the claimed invention. Accordingly, this invention is not limited to what is shown in the drawings and described in the specification but only as indicated in the appended claims. Any numbering or ordering of elements in the following claims is merely for convenience and is not intended to suggest that the ordering of the elements of the claims has any particular significance other than that otherwise expressed by the language of the claims.

What is claimed is:

1. A method for repairing a defect in a muscle wall comprising:
   using a tubular member to create no more than one opening through a muscle wall adjacent to the defect in a ventral surface of the muscle wall, wherein the tubular member does not penetrate a peritoneum;
   inserting an introducer through the opening; and
   conducting tissue repair on the ventral surface of the muscle wall through the introducer.

2. The method of claim 1 further comprising, prior to inserting an introducer through the opening, placing a guidewire using the tubular member, removing the tubular member, and placing a dilator to be used along with the introducer.

3. The method of claim 1 wherein the act of conducting tissue repair comprises inserting a form through the introducer to a position adjacent the defect, wherein the form serves to repair the defect.

4. The method of claim 1 wherein the act of conducting tissue repair comprises inserting a form and depositing a filling material adjacent the form.

5. The method of claim 4 wherein the form comprises a carrier and a prosthesis.

6. The method of claim 5 wherein the carrier is a balloon.

7. The method of claim 5 wherein the prosthesis is a mesh portion.

8. The method of claim 5 wherein the carrier is a balloon and the prosthesis is a mesh portion.

9. The method of claim 4 wherein at least a portion of the form dissolves after the filling material is deposited.

10. The method of claim 1, and further comprising the step of guiding the tubular member to a preperitoneal space using imaging technology.

11. The method of claim 3, wherein the form is a substantially continuous mesh patch.

12. The method of claim 1 wherein the act of conducting tissue repair comprises inserting a mesh adjacent the defect, wherein the mesh serves to repair the defect.

13. A method for repairing a defect in a muscle wall comprising:
using a tubular member to create no more than one opening through a muscle wall adjacent to the defect in a ventral surface of the muscle wall;
using imaging technology to guide the tubular member;
inserting an introducer through the opening; and
inserting a form through the introducer to a position adjacent the defect, wherein the form serves to repair the defect.

14. The method of claim 13 further comprising depositing a filling material adjacent the form.

15. The method of claim 13 wherein the form comprises a carrier and a prosthesis.

16. The method of claim 15 wherein the carrier is a balloon and the prosthesis is a mesh portion.

17. The method of claim 13, wherein the form is a mesh portion.

18. A method for repairing a hernia comprising
using a tubular member to create no more than one opening through a muscle wall to a preperitoneal space, the opening and the preperitoneal space being adjacent to a defect in the muscle wall;
using imaging technology to guide the tubular member;
inserting an introducer through the opening; and
inserting a form through the introducer to a position adjacent to a ventral surface of the defect, wherein the form serves to repair the defect.

19. The method of claim 18, wherein the form comprises a carrier and a prosthesis.

20. The method of claim 19, wherein the carrier is a balloon.

21. The method of claim 19, wherein the prosthesis is a mesh portion.

22. The method of claim 19, wherein the carrier is a balloon and the prosthesis is a mesh portion.

23. The method of claim 18, wherein the method is carried out without producing an open wound, without using multiple trocars and without manual dissection or retraction of tissue.

24. The method of claim 23, wherein at least a portion of the form dissolves after the filling material is deposited.

25. The method of claim 18, wherein the preperitoneal space adjacent to the defect is accessed via a tubular member, wherein an introducer is placed adjacent the defect through the tubular member, and the form is sent to the defect, via the introducer, wherein the peritoneum remains intact.

26. A method for repairing a hernia comprising
using a tubular member to create no more than one penetration in an abdominal wall, the penetration being the only penetration in the abdominal wall through which a device enters a preperitoneal space;
inserting an introducer through the penetration; and
inserting a form through the introducer to a position adjacent to a ventral surface of a defect in the abdominal wall, wherein the form serves to repair the defect.

27. The method of claim 26 wherein the tubular member does not penetrate a peritoneum.

28. The method of claim 26 wherein the penetration is adjacent to the defect.

29. The method of claim 26 further comprising using imaging technology to guide the tubular member.

30. The method of claim 26, wherein the form comprises a carrier and a prosthesis.

31. The method of claim 30, wherein the carrier is a balloon.

32. The method of claim 30, wherein the prosthesis is a mesh portion.

33. The method of claim 30, wherein the carrier is a balloon and the prosthesis is a mesh portion.

34. The method of claim 26 further comprising depositing a filling material adjacent the form.

* * * * *